United States Patent

Schilling et al.

[11] Patent Number: 5,768,938
[45] Date of Patent: Jun. 23, 1998

[54] YARN SENSOR

[75] Inventors: Peter Schilling, Siebnen; Cyrill Bucher, Wallisellen, both of Switzerland

[73] Assignee: Zellweger Luwa AG, Oster, Switzerland

[21] Appl. No.: 709,521

[22] Filed: Sep. 6, 1996

[30] Foreign Application Priority Data

Sep. 6, 1995 [CH] Switzerland ............ 02 523/95

[51] Int. Cl.[6] .................................... G01N 21/89
[52] U.S. Cl. .................. 73/160; 356/430; 356/429
[58] Field of Search .............. 73/160; 356/429, 356/430

[56] References Cited

U.S. PATENT DOCUMENTS 3,712,743  1/1973  Harris et al. ............ 356/430
5,371,584  12/1994  Scheinhütte ............ 356/238
5,414,520  5/1995  Joss et al. ............ 356/430
5,499,794  3/1996  Aeppil ............ 250/559.45
5,521,395  5/1996  Hensel et al. ............ 356/430

FOREIGN PATENT DOCUMENTS 0425015  5/1991  European Pat. Off. .
93/13407  7/1993  WIPO .

*Primary Examiner*—Ronald L. Biegel
*Attorney, Agent, or Firm*—Burns, Doane, Swecker & Mathis, L.L.P.

[57] ABSTRACT

The invention relates to a yarn sensor for scanning a yarn (2), which is moving in its longitudinal direction in a measuring gap (3), with a light beam from a light source (4), having a first receiver (7) for directly transmitted light, at least one second receiver (5, 6) for light reflected by the yarn and one element each (8, 9, 10, 11) for transmitting the light between the measuring gap, the light source and a receiver. To keep the overall size and the external dimensions as small as possible, the optical axes (12–15) of the elements for transmitting the light are disposed together in one plane lying at least approximately at right angles to the yarn.

18 Claims, 3 Drawing Sheets

5,768,938

YARN SENSOR

FIELD OF THE INVENTION

The invention relates to a yarn sensor for scanning a yarn moving in its lengthwise direction through a measuring gap. A light beam from a light source is directed to the yarn. Light not absorbed or reflected by the yarn passes to a first receiver for directly transmitted light, and at least one second receiver for light reflected by the yarn. Elements for transmitting the light may be provided between the measuring gap, the light source and the receiver.

BACKGROUND OF THE INVENTION

WO 93/13407 discloses a yarn sensor in which a receiver for transmitted light and a receiver for reflected light are disposed opposite one another on either side of a measuring gap. On one side of the measuring gap, inlet and outlet prisms for the light are moreover lined up alongside one another, viewed in the direction of the yarn.

A drawback of this known yarn sensor is that the various elements, which are provided for transmitting and introducing light in a locally correct manner, take up a great deal of space. Such yarn sensors are however intended for installation in textile machines where there is often very little space available for them. It may therefore happen that in certain textile machines these known yarn sensors cannot be installed at all.

SUMMARY OF THE INVENTION

The subject matter of the invention is therefore a yarn sensor which takes up only a little space in an outward direction and may also be fitted with a relatively small measuring gap.

According to the invention, this is achieved in that the optical axes of the elements for transmitting light between the yarn and the receivers together lie in one plane, which is situated transversely or preferably at least approximately at right angles to the yarn or which is pierced by the yarn. It is sufficient if two of said optical axes lie in the plane. This arrangement produces in the measuring gap, for example, on one side a window for light for exposing the yarn to light and, situated alongside, windows for receiving reflected light, which actually lie next to the yarn and so may receive only light reflected laterally by the yarn.

The advantages achieved by the invention are in particular that the measuring principle, according to which, for example, impurities or extraneous fibres may be detected in a yarn by evaluating the transmitted light and the reflected light, may be used also with small measuring gaps. In this case, the spatial requirement in the vicinity of the measuring gap may likewise be reduced. Furthermore, the measuring gap may be inserted into a narrow side of the measuring head or yarn sensor, which means that the yarn travels only a short distance in the yarn sensor. A further advantage is that, according to the invention, the measuring gap may be small and so the known self-cleaning effect of the measuring gap by the yarn may be used to good effect. With small measuring gaps, the influence of extraneous light, which may enter through the inlet opening for the yarn, is also reduced. With small measuring gaps, the measuring zone also comes to lie close to the yarn, which increases the measuring accuracy and keeps the measuring zone clean.

BRIEF DESCRIPTION OF THE DRAWINGS

There follows a detailed description of the invention with reference to the accompanying drawings, in which.

DETAILED DESCRIPTION OF PREFERRED EMBODIMENTS

Figure 1:
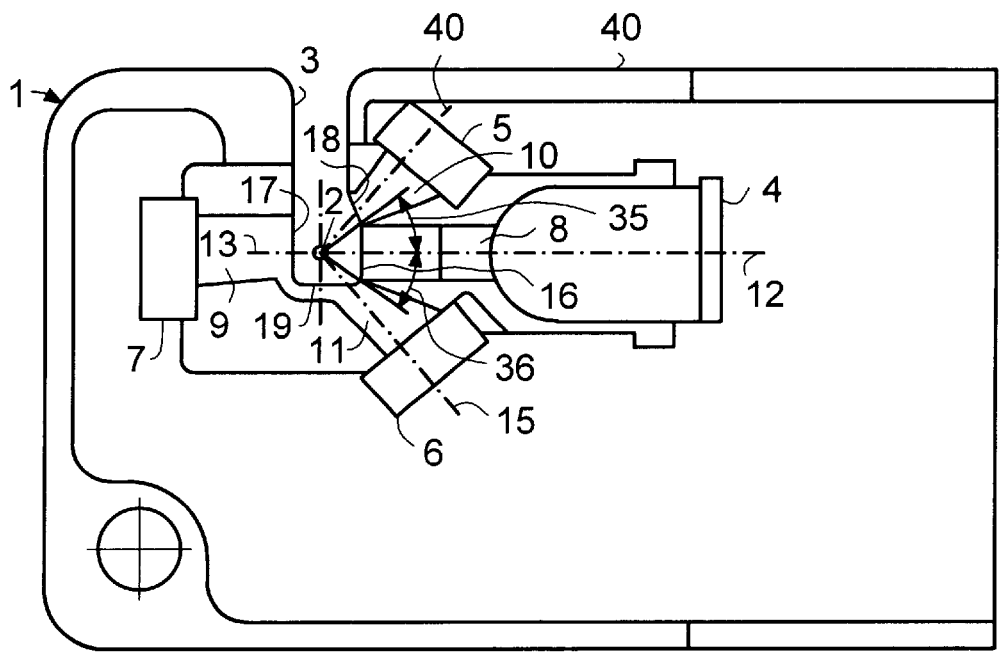
FIG. 1 is a simplified sectional view through part of a yarn sensor.

FIG. 1 is a somewhat simplified sectional view of a yarn sensor 1 for a yarn 2 having a measuring gap 3. Disposed in the vicinity of said measuring gap are a light source 4 and receivers 5 and 6 for reflected light as well as a receiver 7 for transmitted light. The light source 4 and the receivers 5, 6 and 7 are known structural elements and are therefore not described in detail here. Elements 8, 9, 10 and 11 for transmitting the light are disposed between the measuring gap 3, the light source 4 and the receivers 5, 6, 7. These elements 8–11 comprise, for example, a light shaft which is rectangular in cross section and which may be empty or hollow or filled by a light-guiding or transparent body. The walls, which delimit the light shaft, are metallized or designed so as to absorb light. Each of said elements 8–11 has an optical axis 12, 13, 14 and 15, which optical axes preferably intersect in the region of the yarn 2 and of which at least two together define a plane, here the drawing plane, which is situated substantially at right angles to the axis of the yarn 2. The points where the elements 8–11 or their light shafts open into the measuring gap 3 give rise to windows 16, 17, 18 and 19, through which light passes into or out of the measuring gap 3. Filters which limit the spectrum of the light may also be fitted into the elements 8–11. For example, the windows 16 to 19 may take the form of such filters.

Figure 2:
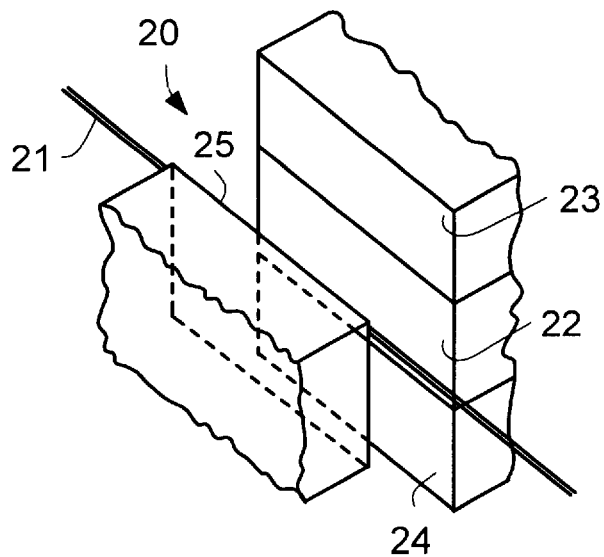
FIG. 2 is a diagrammatic view of part of a measuring gap.

FIG. 2 is a diagrammatic view of part of a measuring gap 20 for a yarn 21, having a window 22 for exposing the yarn 21 to light, windows 23 and 24 for receiving light reflected by the yarn 21 and a window 25 for receiving residual light from the window 22. The residual light is the light which passes out of the window 22 and is not stopped, retained or reflected by the yarn 21. Thus, the window 25 receives the light from the window 22 minus the shadow which the yarn 21 throws onto the window 25. Whereas the windows 22 and 25 are covered by the yarn 21 or lie opposite the yarn 21, the windows 23 and 24 lie right next to the yarn 21 or next to the optical axis 12 of the light source 4 (FIG. 1), when the yarn is viewed approximately at right angles to its direction of motion. FIG. 2 shows the original or homogeneous arrangement of the windows 22–25 relative to one another. In practice it may be advantageous to dispose the window 19 at the bottom of the measuring gap 3, in the manner shown in FIG. 1. The measuring gap 3 may thereby be prevented from extending too far downwards, with the result that the known effect of self-cleaning of the measuring gap by the yarn 2 may be utilized.

Figure 3:
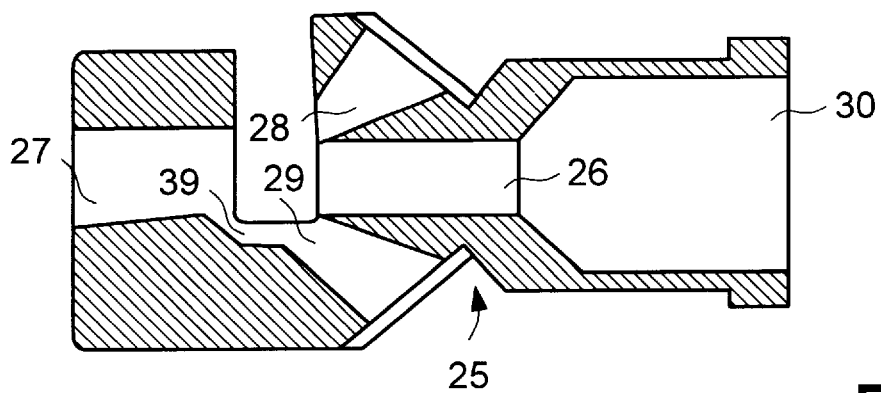
FIGS. 3 and 4 are views of individual parts of the yarn sensor.

FIG. 3 shows a part 25 of the yarn sensor 1 which forms a light shaft 26 for supplied light and light shafts 27, 28 and 29 for light conveyed away from the yarn. The part 25 additionally comprises a location 30 for a light source. The part 25 is of an integral construction so that all of the elements 8–11 for transmitting the light, which are shown in FIG. 1, may be accommodated therein. To this end, a small bridge 39 between the light shafts 27 and 29 is additionally provided here. Conventional receivers are (not shown here) are provided at the outer ends of the light shafts 27, 28 and 29.

Figure 4:
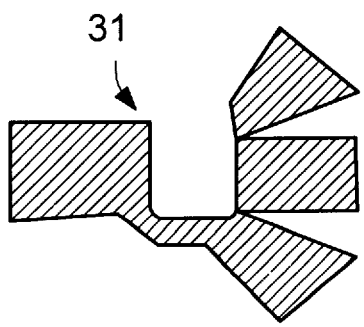

FIG. 4 again shows a light-guiding or light-transmitting body 31, which may be inserted into the part 25 of FIG. 3 and is imagined there in particular as an insert in the light shafts 26 to 29. Thus, a yarn sensor according to the invention may comprise the two parts 25, 31 shown in FIGS. 3 and 4 with the associated receivers and the light source. This arrangement is then to be additionally accommodated in a housing in the manner evident from FIG. 1. The elements for transmitting the light are constructed together in said housing as a single cohesive body 25, 31. By virtue of this arrangement, assembly of the yarn sensor according to the invention is made very much simpler.

Figure 5:
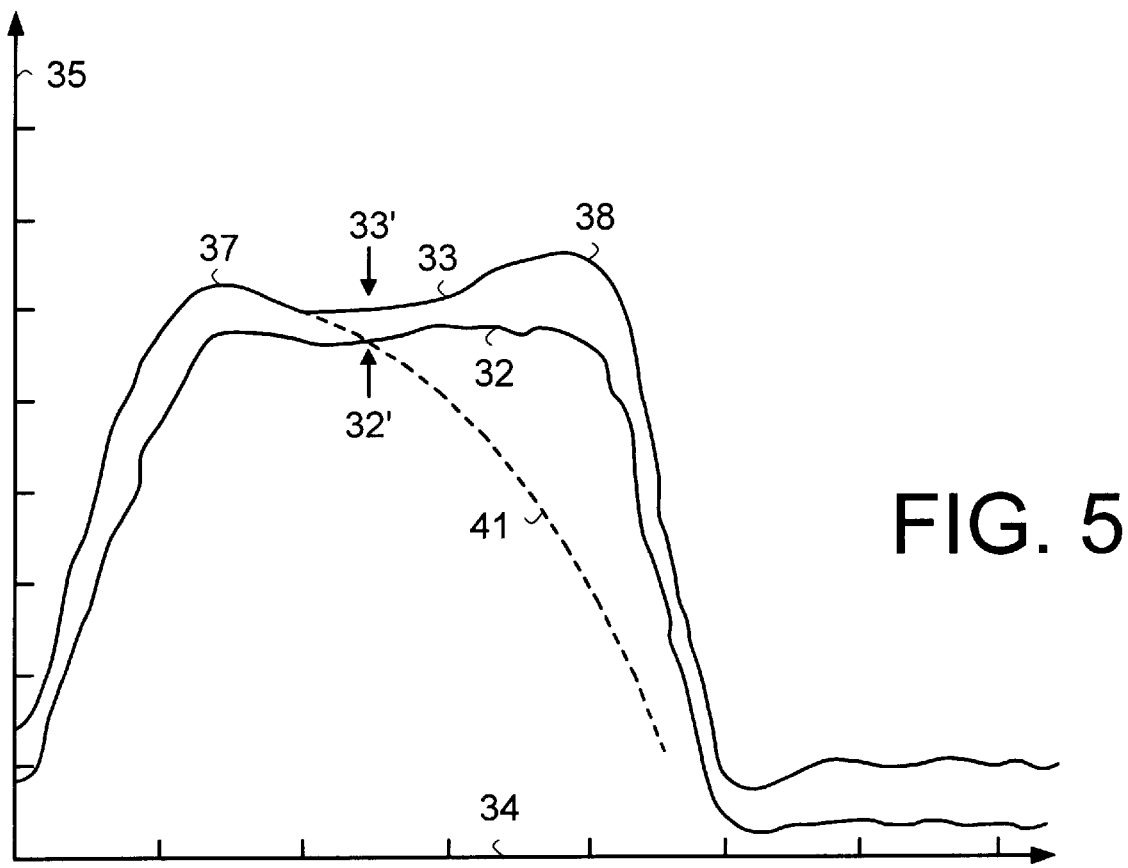
FIG. 5 is a chart showing signal shapes characteristic of a measuring field.

FIG. 5 shows two signal shapes 32, 33 which are recorded above a horizontal axis 34 and alongside a vertical axis 35. Plotted on the horizontal axis 34 are values for a distance corresponding, say, to a distance from the inlet or the lateral boundary surface 40 (FIG. 1) of a measuring gap 3. Plotted on the vertical axis 35 are values of an electric signal of the type supplied by the receivers. Accordingly, the signal shape 32 here indicates which values the receiver for transmitted light measures when the yarn is gradually inserted from above (according to FIG. 1) deeper into the measuring gap 3. The signal shape 33 correspondingly indicates the values which two receivers of reflected light in the arrangement according to FIG. 1 measure in this case. The greatest values are measured when the yarn 2 is roughly in the position shown in FIG. 1. The signal shape 32 then has a region 32' in which the values remain substantially constant. In the signal shape 33 there arises, in the region 33', a possibly rather non-uniform shape which, as will be explained below, is caused by uneven distribution of the reflected light to two receivers. The numeral 41 denotes a signal shape of the type which occurs when only a single receiver for reflected light is provided.

Figure 6:
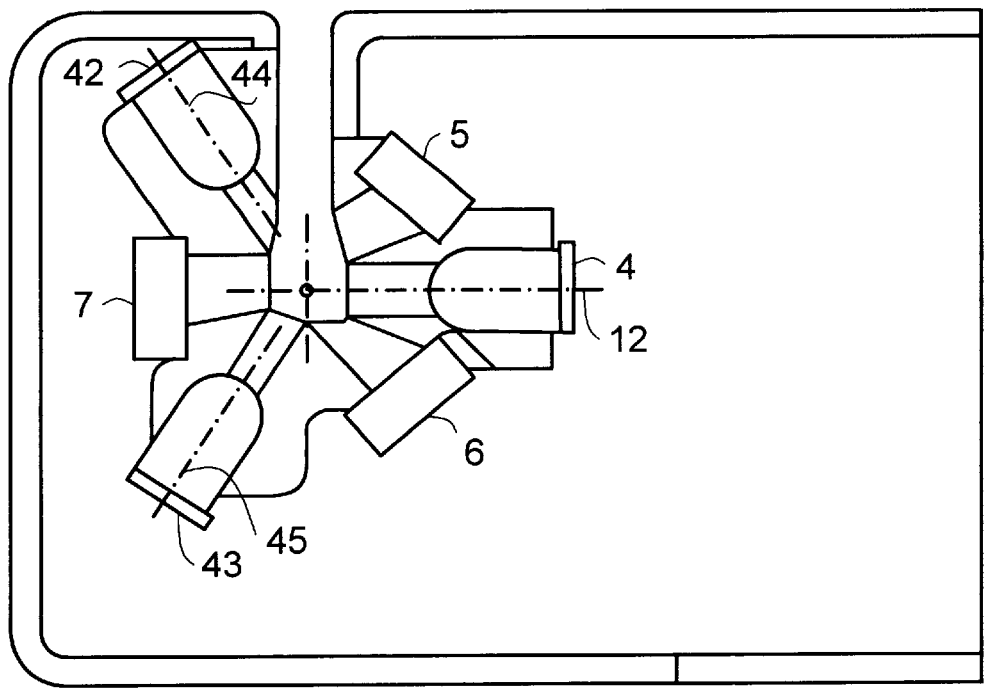
FIG. 6 is a section through part of a further construction of a yarn sensor.

FIG. 6 shows a view of a yarn sensor which includes, besides the light source 4 and the known receivers 5, 6 and 7, two further light sources 42 and 43 with optical axes 44 and 45. The optical axes of the additional light sources 42 and 43 (or of the associated light-transmitting elements) preferably lie in substantially the same plane as the optical axes 12, 13, 14 and 15 described in connection with FIG. 1. It is however also conceivable to position some of the known optical axes in a first plane and some in a second plane.

Figure 7:
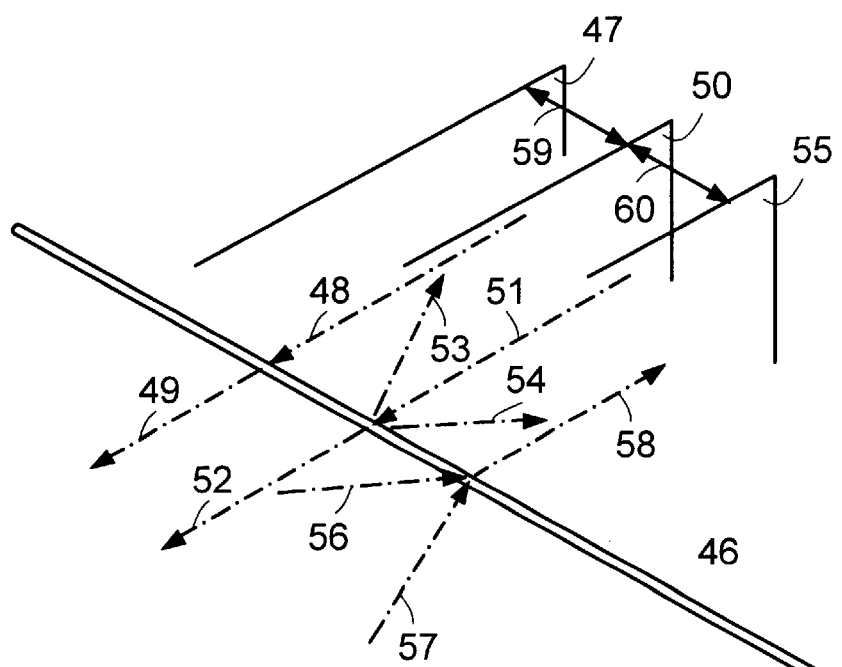
FIG. 7 is a diagrammatic view of possible arrangements of optical axes in a yarn sensor.

FIG. 7 shows a diagrammatic arrangement of a plurality of light sources and receivers adjacent to a yarn 46. Here, the light sources, the receivers and the associated elements for transmitting the light are represented merely by their optical axes. In the arrangement shown by way of example, the optical axis 48 of a light source and the optical axis 49 of a receiver are shown in a first plane 47. Disposed in a second plane 50 spaced apart from the first plane are optical axes 51 of a light source and 52, 53 and 54 of receivers, in a manner already known, say, from FIG. 1. Disposed in a further plane 55 spaced apart from the second plane are the optical axes 56, 57 of two light sources and the optical axis 58 of a receiver. The planes 47, 50 and 55 are preferably approximately parallel to one another and are at distances 59 and 60 which take into account the construction of the elements and the spatial requirement of the elements which are represented here by their optical axes.

The mode of operation of the yarn sensor according to the invention is as follows:

A guide which is known per se and not illustrated here ensures that the yarn 2, as it is drawn in its longitudinal direction in a likewise known manner through the measuring gap 3, stays in the illustrated region in said measuring gap. In the measuring gap 3, the yarn 2 is exposed to the light beam of the light source 4. Light, which does not strike the yarn 2 and is also not sufficiently deflected by the yarn, strikes the receiver 7 and is converted by the receiver into an electric signal. Light reflected by the yarn strikes the receivers 5 or 6 provided it is reflected at a sufficiently large angle 35, 36. The signals from the receivers 5, 6, 7 are then processed in a manner which is known per se and is described, for example, in the cited WO 93/13407.

Should the yarn shift out of its position shown in FIG. 1, the shift has little effect upon the receiver 7 within a specific region, as the signal shape 32 in the region 34 reveals. The receiver 5 receives more reflected light when the yarn 2 is displaced upwards in the measuring gap 3. This circumstance finds expression in the signal shape 33 in the hump 37. The receiver 6 receives more light when the yarn 2 is displaced downwards in the measuring gap 3. This produces a hump 38 in the signal shape 33. Ideally, however, the humps 37 and 38 hardly arise. This may be achieved by correctly tuning the width of the light-transmitting elements 8, 9, 10 and 11 in relation to the yarn diameter and to the position of the yarn 2 in the measuring gap 3, which tuning may be determined for example, by means of experimental arrangements. The slight dip in the signal shape 33 in the region 34 is attributable to the fact that a portion of the light reflected by the yarn 2 is not detected. This portion relates to light which is reflected at an angle smaller than the angles 35 and 36.

The yarn sensor according to the invention may be provided with one or with two or more receivers for reflected light. The construction comprising two receivers 5, 6 or light-transmitting elements 10, 11 disposed symmetrically to the optical axis 12 is however particularly advantageous and gives rise to a more uniform signal shape 33.

In the construction according to FIG. 6, there is the additional possibility of constructing the light sources 4, 42, 43 in such a way that each light source emits a different wavelength. It is therefore possible to recognize whether there is extraneous material such as extraneous fibres or impurities in the yarn. By suitably selecting the emitted light, it is possible to effect a targeted search for specific extraneous materials.

When all of the light sources emit identical light, it is then possible for each light source to be lit for a limited time only and be switched on and off sequentially. Thus, the yarn is exposed to light in each case from a different direction so that it is possible to establish whether the yarn is round or whether it has flat points.

In a construction according to FIG. 7 it is, for example, conceivable to detect a first property of the yarn, e.g. its diameter, in the plane 47. In the plane 50 a second property, e.g. the extraneous material content, may be detected. In the further plane 55 it might be possible, for example, to detect the quality of the surface of the yarn 46 and produce information about it, and so on.

The yarn sensor according to the invention may naturally also be designed and used for other elongated yarn-like formed bodies. The term "yarn sensor" here refers merely to the frequent applications which include detecting extraneous materials or impurities in such a formed body or yarn or indicating other properties such as diameter, uniformity, structure, hairiness etc.

What is claimed is:

1. Yarn sensor (1) for scanning a yarn (2), which is moving in its longitudinal direction in a measuring gap (3), with a light beam from a light source (4), having a first receiver (7) for directly transmitted light, at least one second receiver (5, 6) for light reflected by the yarn and one element each (8, 9, 10, 11) for transmitting the light between the measuring gap, the light source and the receiver, characterized in that the optical axes (13, 14) of at least two elements for transmitting the light are disposed together in one plane lying at right angles to the yarn, and in that the elements for transmitting the light comprise a light shaft (26, 27, 28, 29).

2. Yarn sensor (1) for scanning a yarn (2), which is moving in its longitudinal direction in a measuring gap (3), with a light beam from a light source (4), having a first receiver (7) for directly transmitted light, at least one second receiver (5, 6) for light reflected by the yarn and one element each (8, 9, 10, 11) for transmitting the light between the measuring gap, the light source and the receiver, characterized in that the optical axes (13, 14) of at least two elements for transmitting the light are disposed together in one plane lying at right angles to the yarn, in that the elements for transmitting the light comprise a window (16, 17, 18, 19) directed towards the measuring gap, and in that the windows of the optical elements for transmitting the reflected light to the receiver are situated—viewed at right angles to the direction of motion of the yarn—next to the optical axis (12) of the light source.

3. Yarn sensor (1) for scanning a yarn (2) which is moving in its longitudinal direction in a measuring gap (3), with a light beam from a light source (4), having a first receiver (7) for directly transmitted light, at least one second receiver (5, 6) for light reflected by the yarn and one element each (8, 9, 10, 11) for transmitting the light between the measuring gap, the light source and the receiver, characterized in that the optical axes (13, 14) of at least two elements for transmitting the light are disposed together in one plane lying at right angles to the yarn, and in that the elements for transmitting the light are constructed together as a single, cohesive body (25, 31).

4. Yarn sensor (1) for scanning a yarn (2), which is moving in its longitudinal direction in a measuring gap (3), with a light beam from a light source (4), having a first receiver (7) for directly transmitted light, at least one second receiver (5, 6) for light reflected by the yarn and one element each (8, 9, 10, 11) for transmitting the light between the measuring gap, the light source and the receiver, characterized in that the optical axes (13, 14) of at least two elements for transmitting the light are disposed together in one plane lying at right angles to the yarn, and in that the elements for transmitting the light comprise filters (16, 17, 18, 19) for limiting the spectrum.

5. Yarn sensor (1) for scanning a yarn (2), which is moving in its longitudinal direction in a measuring gap (3), with a light beam from a light source (4), having a first receiver (7) for directly transmitted light, at least one second receiver (5, 6) for light reflected by the yarn and one element each (8, 9, 10, 11) for transmitting the light between the measuring gap, the light source and the receiver, characterized in that the optical axes (13, 14) of at least two elements for transmitting the light are disposed together in one plane lying at right angles to the yarn, and in that further optical axes of further light sources and receivers are situated in further planes (47, 50, 55) which are spaced apart from one another.

6. Yarn sensor (1) for scanning a yarn (2), which is moving in its longitudinal direction in a measuring gap (3), with a light beam from a light source (4), having a first receiver (7) for directly transmitted light, at least one second receiver (5, 6) for light reflected by the yarn and one element each (8, 9, 10, 11) for transmitting the light between the measuring gap, the light source and the receiver, characterized in that the optical axes (13, 14) of at least two elements for transmitting the light are disposed together in one plane lying at right angles to the yarn, and in that further light sources (42, 43) are provided, the optical axes (44, 45) of which are situated in the plane.

7. Yarn sensor according to claim 6, characterized in that the light sources are activated sequentially.

8. Yarn sensor according to claim 5, characterized in that the light sources are activated sequentially.

9. Yarn sensing apparatus for scanning a yarn as the yarn moves in its lengthwise direction through a measuring gap in said yarn sensing apparatus, comprising a light source for emitting light to illuminate said yarn passing through said gap, a first light receiver for receiving from said gap light directly transmitted from said source, at least one second receiver for receiving light reflected by the yarn, and means for transmitting light from the light source to the measuring gap and from the gap to each of said receivers, said means for transmitting light including at least two light transmitting elements having optical axes disposed together in one plane lying at right angles to the yarn and at least one of said elements comprising a light shaft.

10. Yarn sensing apparatus according to claim 9, wherein said means for transmitting light comprises a light conductor constructed as a cohesive body.

11. Yarn sensing apparatus for scanning a yarn as the yarn moves in its lengthwise direction through a measuring gap in said yarn sensing apparatus, comprising a light source for emitting light to illuminate said yarn passing through said gap, a first light receiver for receiving from said gap light directly transmitted from said source, at least one second receiver for receiving light reflected by the yarn, and means for transmitting light from the light source to the measuring gap and from the gap to each of said receivers, said means for transmitting light including at least two light transmitting elements having optical axes disposed together in one plane lying at right angles to the yarn and being constructed together as a single cohesive body.

12. Yarn sensing apparatus according to claim 11 wherein each of said elements comprises a light conductor.

13. Yarn sensing apparatus according to claim 11, wherein at least one of said light transmitting elements comprises a filter for limiting the spectrum.

14. Yarn sensing apparatus according to claim 11, wherein further optical axes of further light sources and receivers are situated in further planes which are spaced apart from one another.

15. Yarn sensing apparatus according to claim 14, wherein the light sources are activated sequentially.

16. Yarn sensing apparatus according to claim 11, wherein further light sources are provided, the optical axes of which are situated in the plane.

17. Yarn sensing apparatus according to claim 16, wherein the light sources are activated sequentially.

18. Yarn sensing apparatus for scanning a yarn as the yarn moves in its lengthwise direction through a measuring gap in said yarn sensing apparatus, comprising a light source for emitting light to illuminate said yarn passing through said gap, a first light receiver for receiving from said gap light directly transmitted from said source, at least one second receiver for receiving light reflected by the yarn, and means for transmitting light from the light source to the measuring gap and from the gap to each of said receivers, said means for transmitting light including at least two light transmitting elements having optical axes disposed together in one plane lying at right angles to the yarn and said elements comprising windows directed toward the measuring gap, with the windows of the optical elements for transmitting reflected light to the receiver being situated—viewed at right angles to the direction of motion of the yarn—next to the optical axis of the light source.

* * * * *